US007067290B2

(12) United States Patent
Regentin et al.

(10) Patent No.: US 7,067,290 B2
(45) Date of Patent: Jun. 27, 2006

(54) METHOD FOR PRODUCTION OF POLYKETIDES

(75) Inventors: Rika Regentin, Hayward, CA (US); Ruchir P. Desai, Foster City, CA (US)

(73) Assignee: Kosan Biosciences Incorporated, Hayward, CA (US)

( * ) Notice: Subject to any disclaimer, the term of this patent is extended or adjusted under 35 U.S.C. 154(b) by 329 days.

(21) Appl. No.: 10/712,897

(22) Filed: Nov. 12, 2003

(65) Prior Publication Data

US 2004/0146992 A1 Jul. 29, 2004

Related U.S. Application Data

(60) Provisional application No. 60/456,811, filed on Mar. 21, 2003, provisional application No. 60/425,552, filed on Nov. 12, 2002.

(51) Int. Cl.
| | |
|---|---|
| C12P 17/06 | (2006.01) |
| C12P 7/42 | (2006.01) |
| C12P 7/26 | (2006.01) |
| C12P 7/62 | (2006.01) |

(52) U.S. Cl. ............... 435/125; 435/75; 435/135; 435/146; 435/148

(58) Field of Classification Search ............... 435/125, 435/146, 135, 75, 148
See application file for complete search history.

(56) References Cited

U.S. PATENT DOCUMENTS

| 5,712,146 A | 1/1998 | Khosla et al. ......... 435/252.35 |
| 5,830,750 A | 11/1998 | Khosla et al. ......... 435/252.35 |
| 5,962,290 A | 10/1999 | Khosla et al. ............... 435/183 |
| 6,033,883 A | 3/2000 | Barr et al. ................... 435/148 |
| 6,080,555 A | 6/2000 | Khosla et al. ................. 435/41 |
| 6,177,262 B1 | 1/2001 | Ziermann et al. ............. 435/76 |
| 6,261,816 B1 | 7/2001 | Khosla et al. ............... 435/183 |
| 6,274,560 B1 | 8/2001 | Khosla et al. ................ 514/29 |
| 6,451,768 B1 | 9/2002 | Chu ............................ 514/29 |
| 6,461,838 B1 * | 10/2002 | Khosla et al. ............. 435/91.1 |
| 6,509,455 B1 | 1/2003 | Ashley et al. ............. 536/23.2 |
| 6,551,802 B1 | 4/2003 | Khosla et al. ................. 435/76 |
| 6,558,942 B1 | 5/2003 | Khosla et al. ......... 435/252.35 |
| 6,562,602 B1 | 5/2003 | Licari et al. ................ 435/123 |
| 2002/0045220 A1 | 4/2002 | Khosla et al. ................. 435/76 |
| 2002/0119937 A1 | 8/2002 | Khosla et al. ................. 514/28 |
| 2002/0137152 A1 | 9/2002 | Santi et al. .................. 435/118 |
| 2004/0014183 A1 | 1/2004 | Licari et al. ................ 435/118 |
| 2004/0018598 A1 * | 1/2004 | Santi et al. .................... 435/75 |

FOREIGN PATENT DOCUMENTS

| WO | WO 00/44717 A2 | 8/2000 |
| WO | WO 01/31035 A2 | 5/2001 |
| WO | WO 01/31049 A2 | 5/2001 |
| WO | WO 02/12534 A2 | 2/2002 |

OTHER PUBLICATIONS

Cortes et al., "Repositioning of a Domain in a Modular Polyketide Synthase to Promote Specific Chain Cleavage," Science 268, 1487-1489 (1995).
Raganathan et al., "Knowledge-based design of bimodular and trimodular polyketide synthases based on domain and module swaps: a route to simple statin analogues," Chem. Biol 6, 731-741 (1999).
Leaf et al., "Employing racemic precursors in directed biosynthesis of 6-dEB analogs," J. Chem. Technol. Biotechnol. 77, 1122-1126 (2002).
Kao et al., "Evidence for Two Catalytically Independent Clusters of Active Sites in a Functional Modular Polyketide Synthase," Biochemistry, 35, 12363-12368 (1996).
Hu et al., "Enhanced heterologous polyketide production in *Streptomyces* by exploiting plasmid co-integration," J. Ind. Microbiol. Biotechnol., 30 (8), 516-522 (2003).
Gokhale et al., "Dissecting and Exploiting intermodular Communication in Polyketide Synthases," Science, 284, 482-485 (1999).
McDaniels et al., "Engineered Biosynthesis of Novel Polyketides," Science, 262, 1546-1550 (1993).
Kieser et al., Practical Streptomyces Genetics, p. 153 (John Innes Foundation, Norwich, UK, 2000).
Kao et al., "Manipulation of Macrolide Ring Size by Directed Mutagenesis of a Modular Polyketide Synthase," J. Am. Chem. Soc., 117, 9105-9106 (1995).
Weissman et al., "Evaluating precursor-directed biosynthesis towards novel erythromycins through *in vitro* studies on a bimodular polyketide synthase," Chem. Biol. 5, 743-754 (1998).
Regentin et al., "Precursor-directed biosynthesis of novel triketide lactones," *Biotechnol Prog.* 20 (1), 122-7 (Jan.-Feb. 2004).

* cited by examiner

*Primary Examiner*—Herbert J. Lilling
(74) *Attorney, Agent, or Firm*—Yuan Chao

(57) ABSTRACT

A method for the production of a polyketide by fermentation comprising the steps of growing a culture of a polyketide-producing organism at a pH value conducive to cell growth for a time sufficient to generate the producing culture, lowering the pH of the culture to a value conducive to polyketide product stability, continuing the fermentation until a maximal titer of polyketide is achieved, and optionally extracting the polyketide from the culture.

17 Claims, 4 Drawing Sheets

METHOD FOR PRODUCTION OF POLYKETIDES

CROSS-REFERENCE TO RELATED APPLICATIONS

This application claims the benefit of U.S. Provisional Application Nos. 60/425,552, filed Nov. 12, 2002, and 60/456,811, filed Mar. 21, 2003, the disclosures of which are incorporated herein by reference.

BACKGROUND OF THE INVENTION

1. Field of the Invention

This invention relates to methods for improving the yields of polyketide products that are unstable under standard fermentation conditions.

2. Description of Related Art

A large variety of polyketides are produced by fermentation. While many of these polyketides are of medical significance per se, they can also serve as starting materials for the chemical synthesis of medicinally important compounds. For example, Santi et al., WO 02/12534 A2 (2002), incorporated herein by reference, discloses the preparation and use of triketide lactones as precursors of complex natural products such as the anti-cancer agents discodermolide and epothilone. The preparation of triketide lactones by fermentation also has been described in Khosla et al., U.S. Pat. No. 5,712,146 (1998) and U.S. Pat. No. 6,080,555 (2000); Cortes et al., *Science* 268: 1487–1489 (1995); and Ranganathan et al., *Chem. Biol.* 6:731–741 (1999).

We have discovered that triketide lactones are unstable under the typical fermentation conditions used for small molecule production, leading to reduced yields of triketide lactones. This invention provides a fermentation method whereby the stability of triketide lactones is increased, thus providing a more economical method for their production.

BRIEF SUMMARY OF THE INVENTION

In one aspect, the present invention provides a method for the production of polyketides by fermentation, comprising the steps of growing a culture of a polyketide-producing organism at a pH value conducive to cell growth for a time sufficient to generate the producing culture, lowering the pH of the culture to a value conducive to polyketide product stability, continuing the fermentation until a maximal titer of polyketide is achieved, and optionally extracting the polyketide from the culture.

In certain embodiments of the invention, the pH value conducive to cell growth is between about pH 5 and about pH 8. In certain other embodiments, the pH value conducive to cell growth is between about pH 6 and about pH 7. In certain other embodiments, the pH value conducive to cell growth is about pH 6.5.

In certain embodiments of the invention, the time sufficient to generate a producing culture is the time required to reach a maximum cell density. In certain other embodiments of the invention, the time sufficient to generate a producing culture is the time required for the culture to reach the end of logarithmic growth. In certain other embodiments of the invention, the time sufficient to generate a producing culture is the time required to begin production of the polyketide.

In certain embodiments of the invention, the pH value conducive to polyketide product stability is between about pH 4 and about pH 7. In certain embodiments of the invention, the pH value conducive to polyketide product stability is between about pH 5 and about pH 6. In certain embodiments of the invention, the pH value conducive to polyketide product stability is about pH 5.5, more preferably about pH 5.25.

In certain embodiments of the invention, the polyketide being produced is a triketide lactone, preferably a triketide lactone having a structure according to formula 1

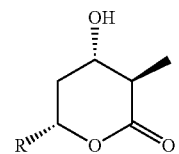

(1)

where R is methyl, ethyl, propyl, vinyl, or chloromethyl. More preferably, the triketide lactone is selected from the group consisting of compounds 2 ("TKL"), 3 ("V-TKL"), and 4 ("CM-TKL"), corresponding respectively to R equals ethyl, vinyl, and chloromethyl in formula 1.

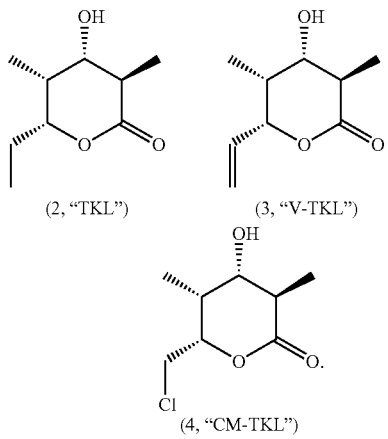

BRIEF DESCRIPTION OF THE DRAWING(S)

FIG. 1 shows the stabilities of V-TKL and CM-TKL in fermentation broth at various pH values.

FIGS. 2A and 2B show the results of pH shift experiments performed in shake flasks. FIG. 2A shows the titers of CM-TKL as a function of fermentation time after addition of diketide and pH shift to the indicated values, after 2 days of growth. FIG. 2B shows the measured pH values in the shake flasks as a function of fermentation time.

DETAILED DESCRIPTION OF THE INVENTION

Many factors influence the final titer of a molecule produced in a fermentation, including the cell density of the producing microorganism, the expression level and specific activities of the relevant biosynthetic enzymes, and the stability of the small molecule under the fermentation conditions. Producing microorganisms typically grow best at pH values near 7, leading to maximal cell densities and levels of biosynthetic enzymes; yet the molecule being produced may be unstable at or above neutral pH values. The present invention provides fermentation methods suitable for maximizing production of such unstable molecules, in particular triketide lactones, which are unstable at or above pH 7.

Figure 1:
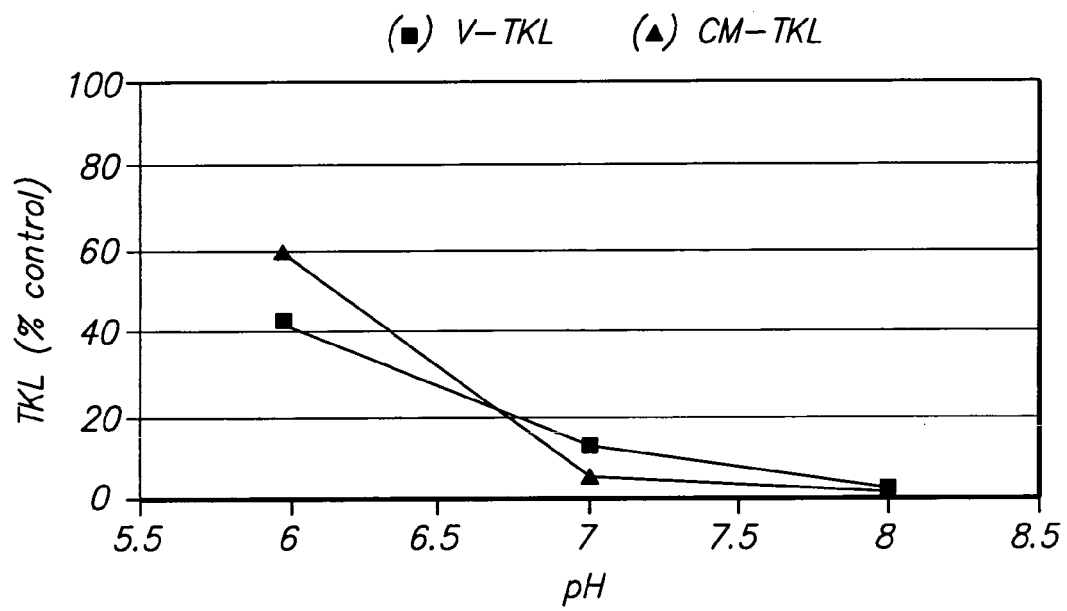

As shown in FIG. 1, triketide lactones such as V-TKL and CM-TKL are unstable in fermentation broth at pH values above 6–8. Investigation by mass spectrometry indicates that the triketide lactones are irreversibly degraded at higher pH values: significant decomposition is noted after 18 h incubation at pH 6 and essentially all the triketide lactone is degraded after 18 h incubation at pH 8. While the triketide lactones are stabilized at low pH values, particularly pH values below 6, the producing organisms, in this case either *Streptomyces coelicolor* or *Escherichia coli*, do not grow well in such acidic environments. The pH-shift method of the present invention provides a solution to the diverging requirements of producing organism growth and product stability.

Figure 2A:
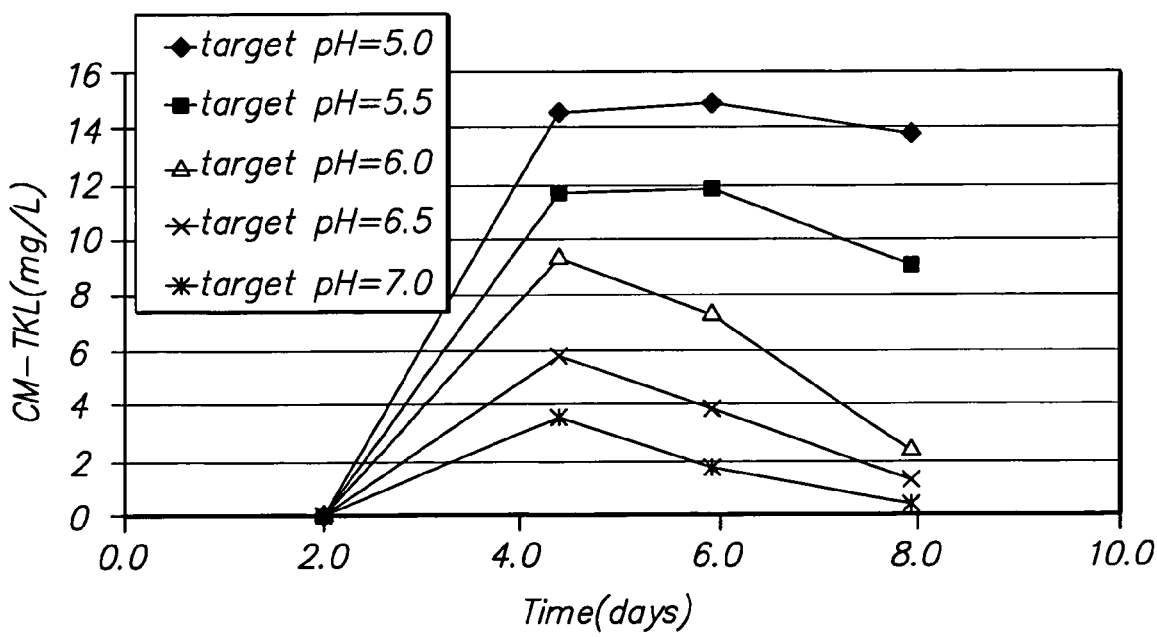
Figure 2B:
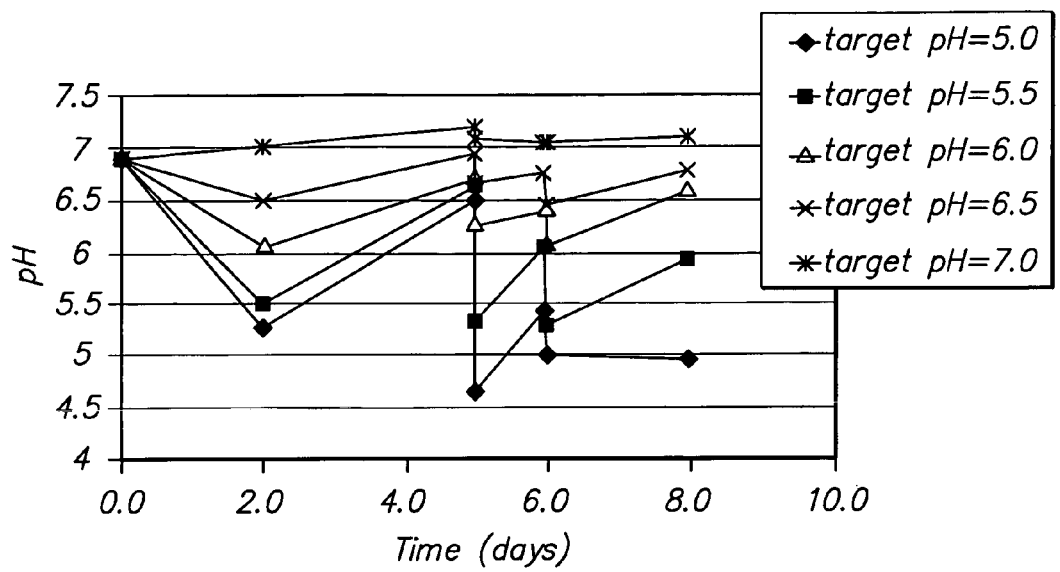

In one embodiment of the invention, described in Example 1 below, a culture of *Streptomyces coelicolor* is used to produce V-TKL and CM-TKL by growing the culture starting at pH 7 for 48 hours, then lowering the pH and initiating triketide lactone production by addition of the appropriate diketide substrate, and continuing the fermentation until maximal product titer is achieved. Suitable strains of *Streptomyces coelicolor* include, for example, K129-187-H, which expresses a mutant form of the first two modules of 6-deoxyerythronolide B synthase (DEBS) fused to the terminal thioesterase, in which the first module ketosynthase is inactivated, and K260-140-1, which expresses the second module of DEBS fused to the terminal thioesterase. Triketide lactone production in these strains is thus dependent upon the feeding of a suitable diketide thioester as described in Khosla et al., U.S. Pat. No. 6,080,555 (2000), incorporated herein by reference. Preparation of diketide thioesters is described in Chu et al., U.S. Pat. No. 6,451,768 (2002), also incorporated herein by reference. Methods for the construction of suitable strains that produce triketide lactones are given in, for example, Khosla et al., U.S. Pat. No. 5,712,146 (1998) and U.S. Pat. No. 5,962,290 (1999), each incorporated herein by reference. The results for different values for the second pH are illustrated in FIG. 2A. FIG. 2B shows the measured pH values in each flask.

Figure 3:
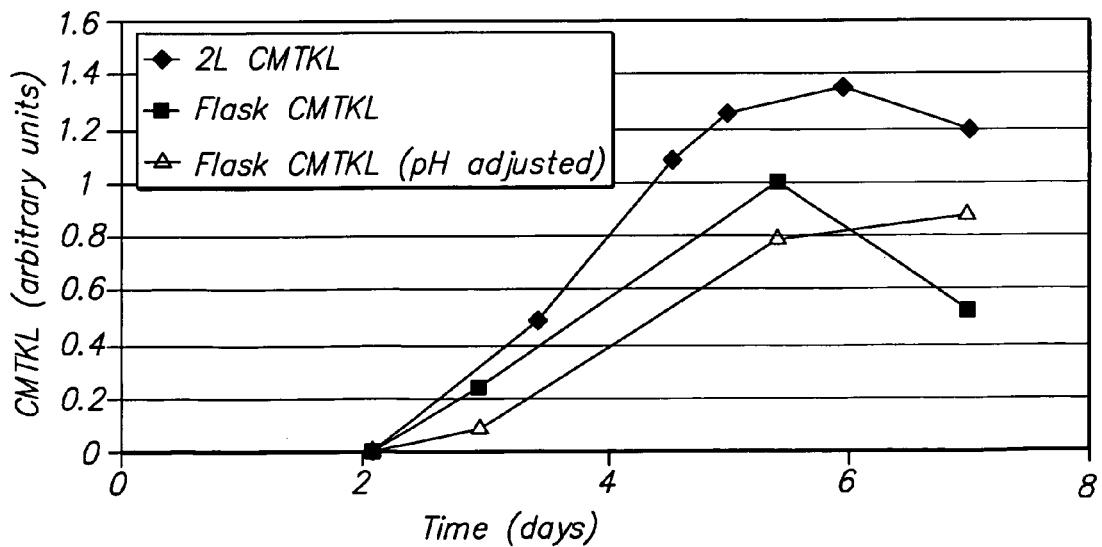
FIG. 3 shows the results of pH shift experiments in fermenters where the pH was adjusted to pH 5.5 compared with shake flask experiments with and without pH shift to pH 5.5.

As described in Example 2 hereinbelow, a 2-L fermenter was run with strain K260-140-1 and with a shift to pH 5.5. The titers were found to be higher than in any flask condition and stable (FIG. 3).

In certain embodiments of the invention, the polyketide-producing organism is a actinomycete, including but not limited to *Streptomyces coelicolor, Streptomyces lividans, Streptomyces hygroscopicus*, and *Saccharopolyspora erythraea*. In certain other embodiments of the invention, the polyketide-producing organism is a eubacterium, including but not limited to *Escherichia coli, Pseudomonas fluorescens, Pseudomonas putida, Pseudomonas aeruginosa, Bacillus subtilis*, and *Bacillus cereus*. In certain other embodiments of the invention, the polyketide-producing organism is a myxobacterium, including but not limited to *Myxococcus xanthus* and *Sorangium cellulosum*. In certain other embodiments of the invention, the polyketide-producing organism is a yeast, including but not limited to *Saccharomyces cerevesiae*. The organism may either be a natural polyketide-producing organism or may be a genetically engineered polyketide producing organism.

One skilled in the art can determine the appropriate time to grow the culture at the pH value conducive to growth. In certain embodiments of the invention, the time sufficient to generate a producing culture is the time required to reach a maximum cell density. Cell density may be determined by any of several methods commonly known in the art, including measurement of light scattering or analysis of cellular protein. In certain other embodiments of the invention, the time sufficient to generate a producing culture is the time required for the culture to reach the end of logarithmic growth. Methods for determining the end of logarithmic growth are commonly known in the art, and typically involve measurement of cell density as a function of time or noting a reduced oxygen demand or carbon dioxide evolution rate. In certain other embodiments of the invention, the time sufficient to generate a producing culture is the time required to begin production of the polyketide. For organisms that produce polyketides without the need for induction or addition of one or more biosynthetic substrates, the onset of polyketide production is readily measured by assay of the fermentation broth, for example using liquid chromatography optionally coupled to mass spectrometry, or by using thin-layer chromatography or bioassay. For organisms that require induction, for example recombinant systems having one or more biosynthetic genes under an inducible promoter, the onset of polyketide production is determined by the time of addition of the inducing stimulus to the fermentation. For organisms that require addition of one or more biosynthetic substrates, for example polyketide synthases having an inactive ketosynthase or an inactive or missing loading domain, the onset of polyketide production is determined by the time of addition of the biosynthetic substrate to the fermentation.

Determination of the optimal pH value for the second phase of fermentation can be determined using the methods described below in Examples 1–5. The pH dependence of polyketide stability is determined by incubating the polyketide in fermentation broth at a set pH and periodically measuring the concentration of remaining polyketide as described in Example 4. The concentration of polyketide may be measured using, for example, liquid chromatography optionally coupled to mass spectrometry as described in Example 3, or by using thin-layer chromatography or bioassay. This information is used to set up a series of shake-flask experiments as described in Example 1. The optimal results from these shake flask experiments are then checked using small-scale fermentation as described in Example 2. In certain embodiments of the invention, the pH value conducive to polyketide product stability is between about pH 5 and about pH 7. In certain embodiments of the invention, the pH value conducive to polyketide product stability is between about pH 5 and about pH 6. In certain embodiments of the invention, the pH value conducive to polyketide product stability is about pH 5.5.

While the present invention is illustrated using triketide lactones, other polyketides are known to be unstable at or above the neutral pH conducive to cell growth. Thus, in certain embodiments of the invention, the polyketide being produced is a triketide lactone. In certain other embodiments of the invention, the polyketide being produced is an analog of ascomycin or FK-506. In certain other embodiments of the invention, the polyketide being produced is an analog of rapamycin. Thus, the following examples are intended to illustrate, not to limit, the invention.

Diketides

Diketides for feeding to producing organisms and making triketide lactones were made as follows. Enantioselective synthesis of (2S,3R)-3-hydroxy-2-methylhexanoate N-acetylcysteamine thioester (5) was performed as described in Weissman et al., *Chem. Biol.*, 5:743–754 (1998), incorporated herein by reference. Enantioselective synthesis of (2S,3R)-3-hydroxy-2-methyl-4-pentenoate N-acetylcysteamine thioester (6, V-SNAC) was performed by the same procedure, except that acrolein was used instead of butyraldehyde.

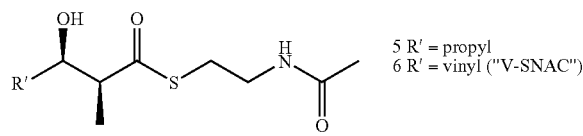

5 R' = propyl
6 R' = vinyl ("V-SNAC")

Diastereoselective synthesis of racemic (2R,3S)-(2S,3R)-3-hydroxy-2-methylhexanoate N-propionylcysteamine thioester (7) was performed as described in Leaf et al., *J. Chem. Technol. Biotechnol.* 77:1122–1126 (2002), incorporated herein by reference. Diastereoselective synthesis of racemic (2S,3S)-4-chloro-3-hydroxy-2-methylbutanoate N-propionylcysteamine thioester (8, "CM-SNPC") was performed by the same procedure, except that chloroacetaldehyde was used instead of butyraldehyde.

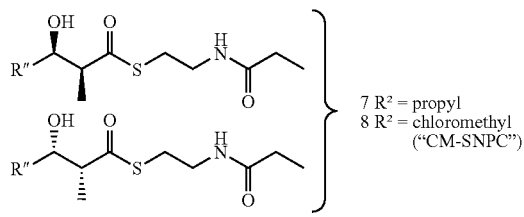

7 R² = propyl
8 R² = chloromethyl ("CM-SNPC")

Additional teachings on synthetic methodology are provided in Santi et al., WO 02/12534 A2 (2002) and Ashley et al., WO 00/44717 A2 (2000), each of which is incorporated herein by reference.

Diketides were prepared as 40% (w/v) solutions in DMSO.

Plasmids and Strains

The following plasmids were used to construct strains. Plasmid pCK16 (Thio$^R$) (Kao et al., *Biochemistry*, 35:12363–12368 (1996)) contains a version of DEBS1+TE in which the active site cysteine of KS1 was replaced by an alanine. Plasmid pBOOST (Apr$^R$) increases plasmid copy number by forming a cointegrate with other plasmids (Hu et al., *J. Ind. Microbiol. Biotechnol.*, 30(8):516–522 (2003)).

Figure 6:
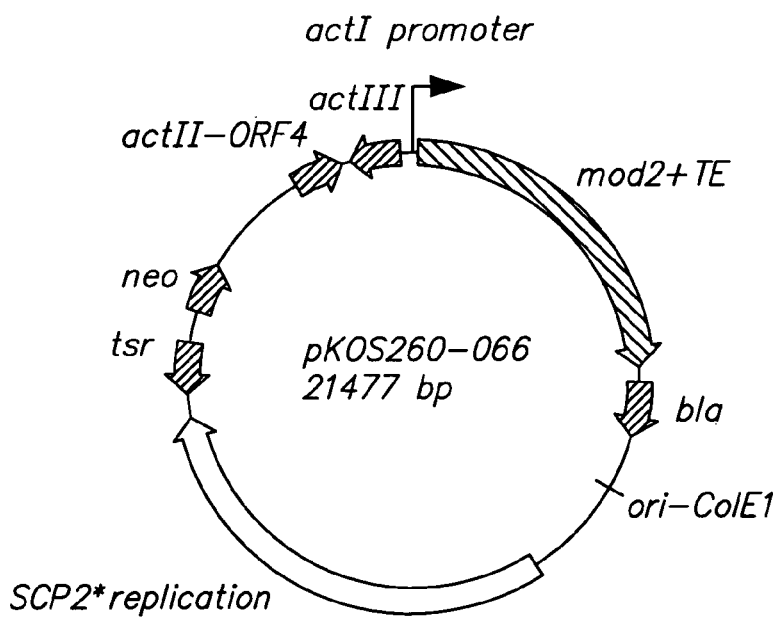
FIG. 6 is a map of plasmid pKOS260-066, described hereinbelow.

The plasmid pKOS214-119, containing module 2 of DEBS1 under the control of the T7 promoter, was constructed as follows. Plasmid pBP175, containing the propionyl-CoA carboxylase genes and module 2 of DEBS1 was digested with NdeI, to remove the propionyl-CoA carboxylase genes, and religated. This plasmid was then digested with XbaI and NdeI, and a synthetic linker introduced to incorporate a PacI restriction site and a consensus ribosome-binding site (RBS) for *Streptomyces* to give pKOS260-063. From this plasmid a PacI-SpeI fragment containing the RBS and module 2 was subcloned into pCK12 (Kao et al., *J. Am. Chem. Soc.*, 117:9105–9106 (1995)), replacing the DEBS1 fragment to give pKOS260-066, which contains module 2+TE (M2+TE) under the control of the actI promoter. The module 2+TE protein expressed contains the initial 39 amino acids from DEBS3 fused to KS2. This arrangement was previously found to be necessary for expression of module 2 with an active KS (Gokhale et al., *Science*, 284:482–485 (1999)). A map of plasmid pKOS 260-066 is shown in FIG. 6.

*S. coelicolor* OP was obtained by removing the complete DEBS genes from a strain mutagenized to overproduce 6-dEB. Plasmid pCK16 and plasmid pBOOST were introduced into *S. coelicolor* CH999 (McDaniels et al., *Science*, 262:1546–1550 (1993); Khosla et al., U.S. Pat. No. 5,830, 750 (1998)) by transformation of protoplasts and selection for apramycin- and thiostrepton-resistant colonies. Strain K129-187-H was selected from these transformants.

Plasmids pCK16 and pBOOST were similarly introduced into *S. lividans* TK24 (Kieser et al., *Practical Streptomyces Genetics*. John Innes Foundation, Norwich, UK, 2000; p 153) to give strain K260-125. Plasmids pKOS260-066 (Thio$^R$), described above, and pBOOST were also introduced into *S. lividans* TK24 to give K260-126.

The plasmids from *S. lividans* strains K260-125 and K260-126 were then transferred to *S. coelicolor* OP by interspecies conjugation (Kieser et al., supra). *S. coelicolor* exconjugants were isolated by plating spores from the conjugation plates onto R5 plates containing apramycin (50 µg/mL) and thiostrepton (12.5 µg/mL), to select for the plasmids, and lincomycin (20 µg/mL) to select for the *S. coelicolor* recipient. *S. coelicolor* OP is derived from *S. coelicolor* CH999 in which the actinorhodin gene cluster has been replaced with the ermE gene encoding resistance to erthromycin and lincomycin. This resulted in strains K260-140 (*S. coelicolor* OP/pKOS260-066/pBOOST) and K260-141 (*S. coelicolor* OP/pCK16/pBOOST). The plasmid and host organism for each strain is summarized in Table 1.

TABLE 1

| Strain (*) | Host | Plasmid |
|---|---|---|
| K129-187-H | *S. coelicolor* CH999 | pCK16 |
| K260-125 | *S. lividans* TK24 | pCK16 |
| K260-126 | *S. lividans* TK24 | pKOS260-066 |
| K260-140 | *S. coelicolor* OP | pKOS260-066 |
| K260-141 | *S. coelicolor* OP | pCK16 |

(*) Additionally, all strains contain pBOOST.

The producing characeristics of the various strains are shown in Table 2.

TABLE 2

| | Triketide Lactone | |
|---|---|---|
| Host | V-TKL (mg/L) | CM-TKL (mg/L) |
| *S. lividans* TK24 | 19 | 7 |
| *S. coelicolor* CH999 | 56 | 18 |
| *S. coelicolor* OP | 107 | 159 |

The effect of using different plasmid constructs and of feeding of different diketides on triketide lactone production by *S. coelicolor* OP is shown in Table 3.

TABLE 3

| Diketide | Triketide Lactone (1) Produced | Plasmid Construct and Product Yield | |
|---|---|---|---|
| | | KS1° (mg/L) | M2 + TE (mg/L) |
| 5 | R = propyl | 410 | 480 |
| 7 | R = propyl | 440 | 500 |
| 6 | R = vinyl | 107 | 183 |
| 8 | R = chloromethyl | 159 | 218 |

Samples of the plasmid pKOS260-066 and *Streptomyces coelicolor* OP were deposited under accession numbers PTA-5606 and PTA5607 respectively, with the American Type Culture Collection (ATCC), P.O. Box 1549, Manassas, Va. 20108, USA, according to the terms of the Budapest Treaty on Oct. 22, 2003.

Media, Methods

Media (Table 4) were prepared by adding all components to 90% of the final volume of water. For SC-VM6-1 and SCFM6-2, the pH was adjusted to 7 with 2.5 N sodium hydroxide. Next, the medium was heated at 70–80° C. until the starch gelatinized (30–45 min) as indicated by visual observation. Finally, the medium was brought up to full volume and autoclaved in 1 L batches at 121° C. for 90 min. SCF3F was pumped into sterilized fermenters from the 1 L bottles.

TABLE 4

| | Formulation | | |
|---|---|---|---|
| Component (g) | SC-VM6-1 | SCFM6-2 | SCF3F |
| Corn starch | 45 | 45 | 45 |
| Brewer's yeast | 10 | 30 | 30 |
| Corn steep liquor | 10 | 20 | 20 |
| Calcium carbonate | 1 | 1 | 1 |
| HEPES, free acid | 23.8 | 23.8 | 0 |
| Maltodextrin DE 7 | 0 | 30 | 60 |
| Glycerol | 8 | 0 | 0 |
| Purified deionized water | Up to 1 L | Up to 1 L | Up to 1 L |

All components were from Sigma Chemical Co. except for deionized water and maltodextrin DE 7 (Cerestar).

To generate cell banks, spores were transferred into 250 mL baffled flasks containing 50 mL of SC-VM6-1 medium with 50 mg/L of thiostrepton and 50 mg/L of apramycin. Several drops of 50% Antifoam B (J T Baker) were added. After 3 days of growth at 30° C., 2 parts of culture were combined with 1 part of sterile 90% glycerol, and 1 mL aliquots of the mixture were transferred into cryovials and frozen at −80° C.

EXAMPLE 1

Shake Flask Protocol

One cell bank vial was used to inoculate 50 ml of SCVM6-1 medium containing 50 mg/L apramycin and 50 mg/L thiostrepton. The seed flask was grown for 3 days at 30° C., then used to inoculate production flasks at 5% (v/v). Production flasks contained 35 ml of SCFM6-2 medium. Cultures were grown for two days and then fed a sterile solution of 400 g/L diketide in DMSO to a final concentration of either 2 g/L racemic diketide (7 or 8) or 1 g/L optically pure diketide (5 or 6). Flasks were harvested 7–8 days after inoculation, with assay samples taken every other day after diketide feeding. For flask experiments with pH shifts, the flask pH was adjusted downward with sterile 2.5 N $H_2SO_4$, or adjusted up with sterile 2.5 N NaOH, immediately prior to addition of diketide. The pH was periodically adjusted to maintain the target pH. All seed and production flasks were prepared with several drops of 50% Antifoam B. Production cultures were run in duplicate, with titers reported as averages.

Results from experiments wherein the pH was adjusted to 5.0, 5.5, 6.0, 6.5, or 7.0 immediately prior to addition of diketide are shown in FIG. 2A.

EXAMPLE 2

Bioreactor Protocol

Bioreactor (fermenter) seeds were started in the same manner as shake flask seeds (Example 1). The 50 ml culture was grown for 2 days then used to inoculate 500 mL of SCVM6-1 medium with 50 mg/L apramycin and 50 mg/L thiostrepton in a 2.8 L Fernbach flask. The culture was grown for two days at 30° C., then used to inoculate 2 L or 5 L fermenters at 5% (v/v).

The production bioreactors (Biostat B 2 L or MD5, B. Braun) were prepared with 1.5 L of SCF3F medium and maintained at a temperature of 30° C. The pH was controlled automatically at pH 6.5 with 2.5 N sulfuric acid or sodium hydroxide unless noted otherwise. Dissolved oxygen (DO) was controlled above 30%, preferably at 50%, with agitation (600–1200 RPM), airflow (0.67 to 2.0 vvm) and oxygen enrichment (0–100%) except where noted otherwise. Foaming was controlled by automatic addition of Antifoam B (J T Baker). The pH was adjusted and diketide was fed approximately 48 hours after inoculation to a final concentration of 2 g/L except as noted otherwise. The bioreactors were harvested after seven days. Results from an experiment wherein the pH was adjusted to pH 5.5 immediately prior to addition of diketide are shown in FIG. 3.

Figure 4:
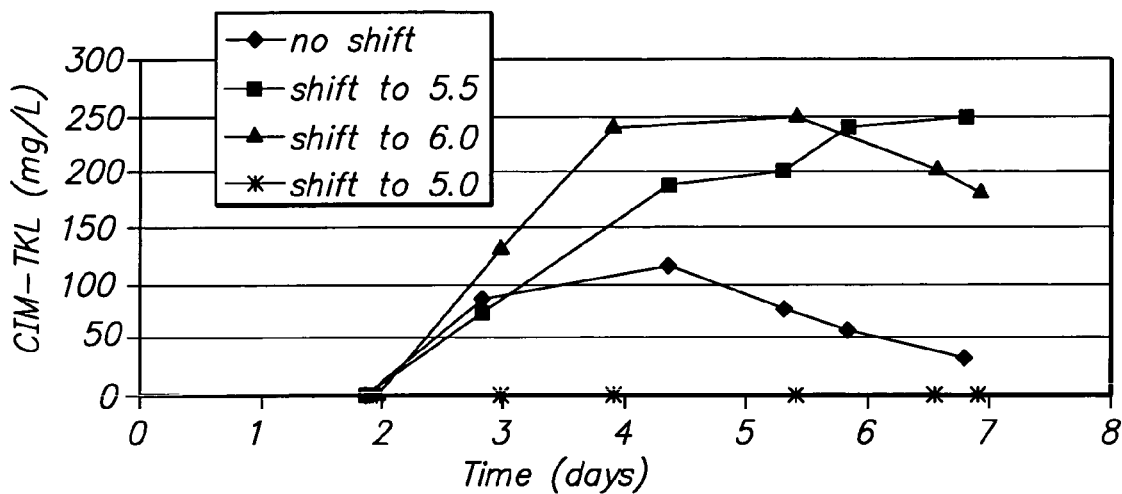
FIG. 4 shows the results of pH shift experiments in fermenters where the pH was adjusted to the indicated values before addition of diketide at day 2.

FIG. 4 shows results from an experiment run in 2-L fermenters, with dissolved oxygen being controlled at 50% with a stirring and airflow cascade (600–1200 rpm and 0.75–2 vvm). The pH was maintained at 6.5 during the initial growth phase by automatic addition of sulfuric acid and sodium hydroxide. Flasks and fermenters were inoculated at 5% and allowed to grow for 2 days. The pH was adjusted as indicated in the figure, and production of polyketide was initiated at that time by addition of diketide.

EXAMPLE 3

Product Analysis

Samples were centrifuged to remove cells and insoluble media components. If necessary, supernatants were diluted in 1:1 acetonitrile-water with 0.1% acetic acid. Samples were analyzed by HPLC-MS/MS, quantitating by comparison with an internal analytical standard of 2,4-dimethyl-3-hydroxyoctanoic acid δ-lactone ("P-TKL"). In cases where the purity of the analytic standard was doubtful, titers were renorted as arbitrary units. Samples were injected onto a $C_{18}$ reversed-phase HPLC column and eluted with a gradient of acetonitrile in water containing 0.1% formic acid. Triketide lactones were detected using multiple reaction monitoring of the following MS/MS transitions: TKL: m/z 173 to 109; CM-TKL: m/z 193 to 119; V-TKL: m/z 171 to 107; and P-TKL: m/z 181 to 123.

The following analytical information for CM-TKL is illustrative: ESI-TOF-MS $[M+H]^+$ 193.0645 (calcd for $C_8H_{14}^{35}ClO_3$, 193.0626); $^1H$ NMR ($CDCl_3$, 400 MHz) δ 4.41 (ddd, J=8.0, 6.5, 2.5 Hz, 1H), 3.83 (dd, J=10.0, 4.0 Hz, 1H), 3.70 (dd, J=11.5, 6.5 Hz, 1H), 3.53 (dd, J=11.5 8.0 Hz, 1H), 2.51–2.44 (m, 2H), 1.38 (d, J=7.0 Hz, 3H), 0.97 (d, J=7.0 Hz, 3H); $^{13}$C NMR (CDCl$_3$, 100 MHz) δ 173.3, 79.0, 72.4, 42.2, 39.6, 34.7, 14.0, 4.1.

EXAMPLE 4 pH Stability of Triketide Lactones

To test the stability of CM-TKL and V-TKL in fermentation supernatant, the following experiment was undertaken. Supernatant from flask cultures was collected at the end of an experiment by centrifugation at 2700×g for 20 minutes. The supernatant was divided into four portions. The pH of the control portion was adjusted to 3.5, and that sample was frozen at −20° C. The remaining portions were adjusted to pH 6,7, and 8 with 2.5 N sodium hydroxide or 2.5 N sulfuric acid and sterilized by filtration. The samples were incubated for 18 hours at 30° C. then analyzed for product as described previously with the data reported as percent of the control. TKL degradation in fermentation supernatants was found to be pH dependent (FIG. 1).

EXAMPLE 5

Titer Optimization

Figure 5A:
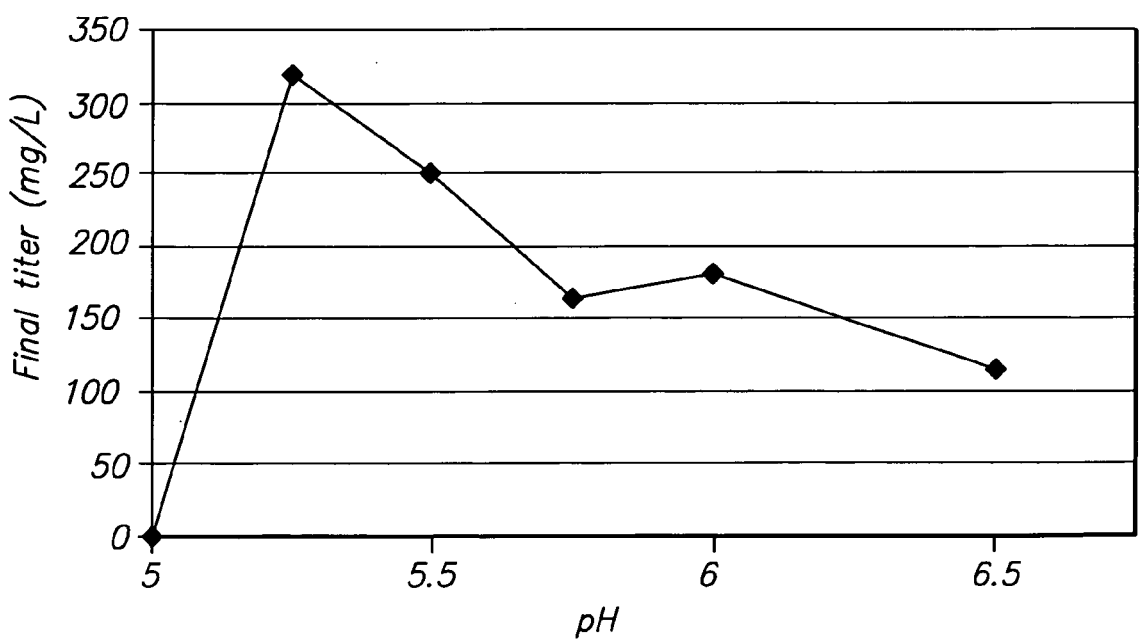
FIG. 5A shows the effect of pH on final product titer.
Figure 5B:
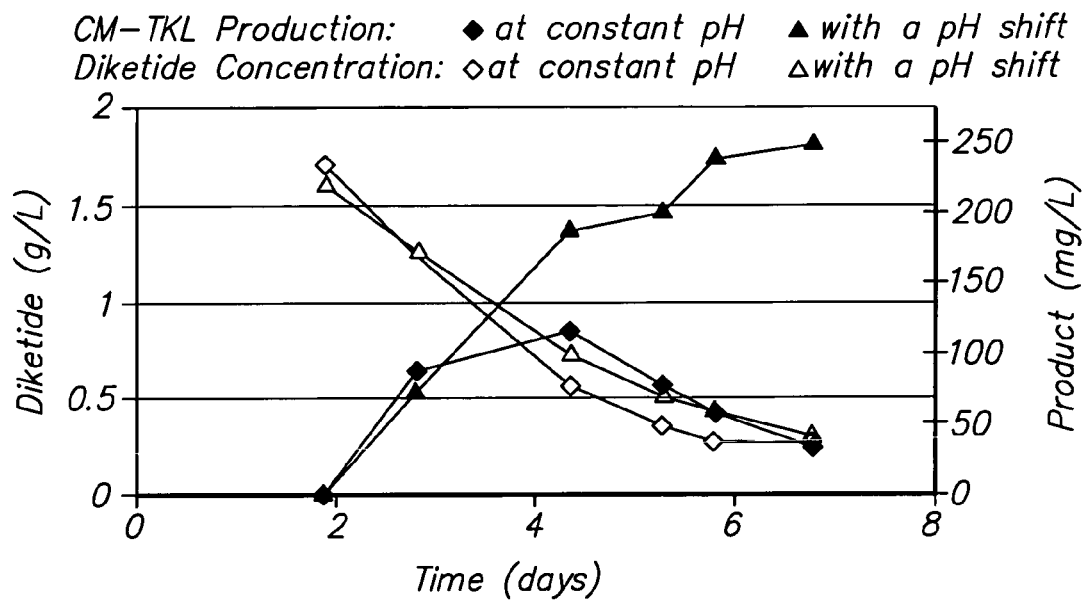
FIG. 5B shows the concentration of diketide precursor and product titer as a function of fermentation time.

The optimal pH for growth of the S. coelicolor OP strain is 6.5. At this pH, the loss of V-TKL and CM-TKL would be 60–70% in 18 h (v. supra). While a pH shift to a lower pH during the course of the fermentation stabilized the triketide lactone products, a shift to pH 5.0 was found to be toxic to S. coelicolor OP cells: the oxygen demand decreased to zero and no product was formed. Final titers increased when the pH was shifted to values between 5.25 and 6.0, with the highest final titer achieved with a shift to pH 5.25 (FIG. 5A). FIG. 5B shows a typical production profile for 2-L bioreactors with and without a pH shift to 5.5. Titers were about double in the bioreactor with the pH shift compared to a bioreactor run at constant pH 6.5 and the product was much more stable. The diketide concentration profile was similar in the two fermentations.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

What is claimed is:

1. A method for the production of a polyketide by fermentation, comprising the steps of growing a culture of a polyketide-producing organism at a pH value conducive to cell growth for a time sufficient to generate the producing culture between about pH 6 and about pH 7, lowering the pH of the culture to a value conducive to polyketide product stability between about pH 5 and about pH 6, continuing the fermentation until a maximal titer of polyketide is achieved, and optionally extracting the polyketide from the culture.

2. The method of claim 1 wherein the pH value conducive to cell growth is about pH 6.5.

3. The method of claim 1 wherein the time sufficient to generate a producing culture is the time required to reach a maximum cell density.

4. The method of claim 1 wherein the time sufficient to generate a producing culture is the time required for the culture to reach the end of logarithmic growth.

5. The method of claim 1 wherein the time sufficient to generate a producing culture is the time required to begin production of the polyketide.

6. The method of claim 1 wherein the pH value conducive to polyketide product stability is about pH 5.5 to about pH 6.0.

7. The method of claim 1 wherein the polyketide-producing organism is an actinomycete.

8. The method of claim 7 wherein the actinomycete is Streptomyces coelicolor, Streptomyces lividans, Streptomyces hygroscopicus, or Saccharopolyspora erytlzraea.

9. The method of claim 1 wherein the polyketide-producing organism is an eubacterium.

10. The method of claim 9 wherein the eubacterium is Escherichia coli, Pseudomonas fiucrescens, Pseudomonas putida, Pseudomonas aeruginosa, Bacillus subtilis, or Bacillus cereus.

11. The method of claim 1 wherein the polyketide-producing organism is a myxobacterium.

12. The method of claim 11 wherein the myxobacterium is Myxococcus xanthus or Sorangium cellulosum.

13. The method of claim 1 wherein the polyketide-producing organism is a yeast.

14. The method of claim 13 wherein the yeast is Saccharomyces cerevesiae.

15. The method of claim 1 wherein the polyketide produced is a triketide lactone.

16. The method of claim 15, wherein the triketide lactone has a structure according to the formula

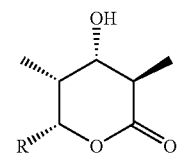

wherein R is methyl, ethyl, propyl, vinyl, or chloromethyl.

17. The method of claim 15 wherein the triketide lactone is selected from the group consisting of

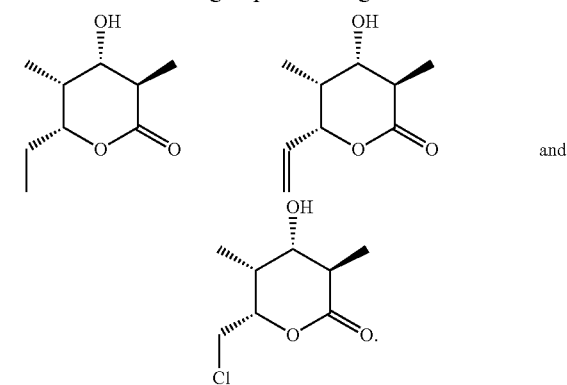

* * * * *